(12) United States Patent
Rizoiu et al.

(10) Patent No.: US 8,221,117 B2
(45) Date of Patent: Jul. 17, 2012

(54) PROBES AND BIOFLUIDS FOR TREATING AND REMOVING DEPOSITS FROM TISSUE SURFACES

(75) Inventors: Ioana M. Rizoiu, San Clemente, CA (US); Jeffrey W. Jones, Robertson, WY (US); Peter Chueh, Irvine, CA (US)

(73) Assignee: BIOLASE, Inc., Irvine, CA (US)

( * ) Notice: Subject to any disclaimer, the term of this patent is extended or adjusted under 35 U.S.C. 154(b) by 600 days.

(21) Appl. No.: 12/234,593

(22) Filed: Sep. 19, 2008

(65) Prior Publication Data

US 2009/0075229 A1 Mar. 19, 2009

Related U.S. Application Data

(60) Provisional application No. 60/995,759, filed on Sep. 28, 2007, provisional application No. 60/994,891, filed on Sep. 21, 2007, provisional application No. 60/994,723, filed on Sep. 20, 2007, provisional application No. 60/994,571, filed on Sep. 19, 2007.

(51) Int. Cl.
*A61C 1/00* (2006.01)

(52) U.S. Cl. .......................................... 433/81; 433/224

(58) Field of Classification Search .................... 433/29, 433/216, 224, 81
See application file for complete search history.

(56) References Cited

U.S. PATENT DOCUMENTS

| | | | | |
|---|---|---|---|---|
| 4,480,996 A | * | 11/1984 | Crovatto | 433/164 |
| 4,940,411 A | * | 7/1990 | Vassiliadis et al. | 433/215 |
| 4,979,900 A | * | 12/1990 | Okamoto et al. | 433/224 |
| 5,151,029 A | * | 9/1992 | Levy | 433/29 |
| 5,570,182 A | | 10/1996 | Nathel et al. | |
| 5,651,783 A | | 7/1997 | Reynard | |
| 5,707,368 A | | 1/1998 | Cozean et al. | |
| 5,800,165 A | * | 9/1998 | Kirsch et al. | 433/29 |
| 5,968,039 A | * | 10/1999 | Deutsch et al. | 606/17 |
| 6,251,103 B1 | | 6/2001 | Berlin | |
| 6,343,929 B1 | * | 2/2002 | Fischer | 433/81 |

(Continued)

FOREIGN PATENT DOCUMENTS

JP 5200045 A 8/1993

(Continued)

OTHER PUBLICATIONS

International Search Report, Dec. 15, 2008, PCT/US2008/077135.

*Primary Examiner* — Ralph Lewis
(74) *Attorney, Agent, or Firm* — Stout, Uxa, Buyan & Mullins, LLP

(57) ABSTRACT

An endodontic probe is used to perform disinfection procedures on target tissues within root canal passages and tubules. The endodontic probe can include an electromagnetic radiation emitting fiber optic tip having a distal end and a radiation emitting region disposed proximally of the distal end. According to one aspect, the endodontic probe can include a porous structure that encompasses a region of the fiber optic tip excluding the radiation emitting region and that is loaded with biologically-active particles, cleaning particles, biologically-active agents, or cleaning agents for delivery from the porous structure onto the target tissues. Another aspect can include provision of the endodontic probe with an adjustable channel-depth indicator, which encompasses a region of the fiber optic tip besides the radiation emitting region and which is movable in proximal and distal directions along a surface of the fiber optic tip to facilitate the provision of depth-of-insertion information to users of the endodontic probe.

20 Claims, 11 Drawing Sheets

U.S. PATENT DOCUMENTS

| | | | |
|---|---|---|---|
| 6,669,685 B1 | 12/2003 | Rizoiu et al. | |
| 7,040,892 B2 * | 5/2006 | Hirszowicz et al. | 433/29 |
| 7,125,254 B2 * | 10/2006 | Calvert | 433/224 |
| 7,470,124 B2 * | 12/2008 | Bornstein | 433/29 |
| 2003/0100824 A1 | 5/2003 | Warren et al. | |
| 2003/0199860 A1 | 10/2003 | Loeb et al. | |
| 2006/0281042 A1 | 12/2006 | Rizoiu et al. | |

FOREIGN PATENT DOCUMENTS

| | | |
|---|---|---|
| JP | 5506601 A | 9/1993 |
| JP | 11511386 A | 10/1999 |
| WO | 8903202 A2 | 4/1989 |

* cited by examiner

| SAPPHIRE TIPS GUIDE | | | | | | |
|---|---|---|---|---|---|---|
| TIP TYPE | MG4 MG6 | MT4 | MS75 | MC6 | MC3 | MC12 |
| INPUT DIA, mm | 0.750 | 0.750 | 0.750 | 1.20 | 1.20 | 1.20 |
| LENGTH, mm | 4,6,9 | 6 | 6 | 6,9 | 9 | 9 |
| OUTPUT DIA, mm | 0.600 | 0.400 | 0.750 | 0.600 | 1.20 / 0.30 | 1.20 |
| SPOT @ 1mm | ○ | ○ | ○ | ○ | ○ ○ | ○ |
| CUT IN DE NT IN @ 4W | V | V 2.5W | V | V | V V | V |

PROBES AND BIOFLUIDS FOR TREATING AND REMOVING DEPOSITS FROM TISSUE SURFACES

This application claims the benefit of Prov. App. 60/995,759, filed on Sep. 28, 2007, Prov. App. 60/994,891, filed on Sep. 21, 2007, Prov. App. 60/994,723, filed on Sep. 20, 2007, and Prov. App. 60/994,571, filed on Sep. 19, 2007, the contents of all which are expressly incorporated herein by reference. This application is related to U.S. application Ser. No. 12/142,656, filed on Jun. 19, 2008, U.S. application Ser. No. 11/800,184, filed on May 3, 2007, Prov. App. 12/020,455, filed on Jan. 25, 2008, and U.S. application Ser. No. 11/033,441, filed on Jan. 10, 2005, the entire contents of all which are incorporated herein by reference.

BACKGROUND OF THE INVENTION

1. Field of the Invention

The present invention relates generally to electromagnetic radiation procedural devices and, more particularly, to the use of electromagnetic radiation devices in medical applications.

2. Description of Related Art

A primary causative agent in pulpal and periapical pathosis is inadequate bacteria control. Research has shown that the absence of infection before obturation of a tooth undergoing endodontic treatment can result in a higher success rate, thus indicating the control or elimination of such intracanal pathogens to be advantageous to the generation of a favorable outcome for a given procedure.

The prior art has encompassed various endodontic treatments directed to the attenuation of bacterial counts and adverse symptoms from the root canal system, many being implemented in a relatively nonsurgical or low impact fashion. Typically, clinical endodontic procedures have relied on mechanical instrumentation, mechanical intracanal irrigants, and medicaments to disinfect the root canal system.

Prior-art instrumentation techniques involving hand and/or rotary instruments, as well as ultrasonic and sonic devices, have brought about some success in reducing bacterial loads in infected canals. While such instrumentation techniques of the prior art have not been altogether ineffective, they do tend to fall short of the goal of total or near total disinfection of the root canal system.

In the category of irrigants, agents such as sodium hypochlorite and chlorhexidine have been implemented in root canal disinfecting treatments with some degree of success. Such agents have been found to be capable, for example, of providing relatively useful antimicrobial effects in certain instances. Here, too, infection of the root canal and adjacent dentin my persist, however, following such applications, owing perhaps to an inability of these agents to reach all the infecting microorganisms.

Regarding the third mentioned category, of medicaments, the use of intracanal medications, such as calcium hydroxide, has typically been ineffective in the context of short-term applications. That is, longer term applications have frequently been indicated as a consequence, for example, of such agents failing to adequately address and eliminate endodontic infections by way of only a few applications. Consequently, such applications in the prior-art have typically required multiple applications, which in turn have required multiple patient visits. These multiple visits, while potentially increasing a rate of effective treatments in connection with medicaments such as calcium hydroxide, can increase treatment time and reduce patient compliance, thus increasing the risk of treatment failure.

Lasers, such as mid-infrared lasers including the Erbium, chromium:yttrium-scandiumgallium-garnet (Er,Cr:YSGG) laser, have been used in root canal procedures involving cleaning, shaping and enlarging of the root canal, as well as in osseous, apical and periodontal surgical procedures. The Er,Cr:YSGG laser is known to be capable of removing calcified hard tissues by emitting a beam of infrared energy at 2.78 µm in combination with an emitted water spray.

SUMMARY OF THE INVENTION

A laser having a high absorption for one or more predetermined fluids, which are disposed either around or adjacent to a target tissue or disposed within the target tissue, is implemented to achieve intra-passage or intracanal disinfection. The fluid can comprise water in typical applications, and the target tissue can comprise soft tissue such as that of a root canal wall in exemplary implementations of the invention. The laser can be operated to clean or disinfect tissue within the root canal in one mode in which an external source applies fluid to or in a vicinity of the target tissue or in another mode in which external fluid is not applied, the latter mode being capable of potentiating an effect of absorption of the laser energy or greater absorption of the laser energy by fluids within bacteria on or in the target tissue. In accordance with another feature of the present invention, radially emitting laser tips are used in the implementation of cleaning and disinfecting procedures of root canals. The radially emitting or side firing effects provided by these laser tips can facilitate, among other things, better coverage of the root canal walls in certain instances as compared, for example, to conventional, forward firing tips. Consequently, a probability that the emitted laser energy will enter dentinal tubules of the root canal can be augmented, thus increasing a disinfecting potential or efficacy of the system, whereby disinfection or cleaning of portions of dentinal tubules disposed at relatively large distances from the canal can be achieved or achieved more efficiently (e.g., during a smaller time window) or more reliably (e.g., yielding results with greater reproducibility).

According to one aspect of the present invention, an endodontic probe is used to perform disinfection of target tissues within root canal passages and tubules. The endodontic probe can comprise an electromagnetic radiation emitting fiber optic tip having a distal end and a radiation emitting region disposed proximally of the distal end, and can further comprise a porous structure which encompasses a region of the fiber optic tip excluding the radiation emitting region and/or which comprises a material that is transparent to a wavelength of energy carried by the electromagnetic radiation emitting fiber optic tip. The porous structure can be loaded with biologically-active particles, cleaning particles, biologically-active agents, and/or cleaning agents that are structured to be delivered from the porous structure onto the target tissues.

Another feature of the present invention includes an endodontic probe for performing disinfection of target tissues within root canal passages and tubules, the endodontic probe comprising (a) an electromagnetic radiation emitting fiber optic tip having a distal end and a radiation emitting region disposed proximally of the distal end and (b) an adjustable channel-depth indicator encompassing a region of the fiber optic tip besides the radiation emitting region. The adjustable channel-depth indicator can be configured to be movable in proximal and distal directions along a surface of the fiber optic tip to provide, for example, depth-of-insertion information to a user of the endodontic probe.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE INVENTION

Figure 1A:
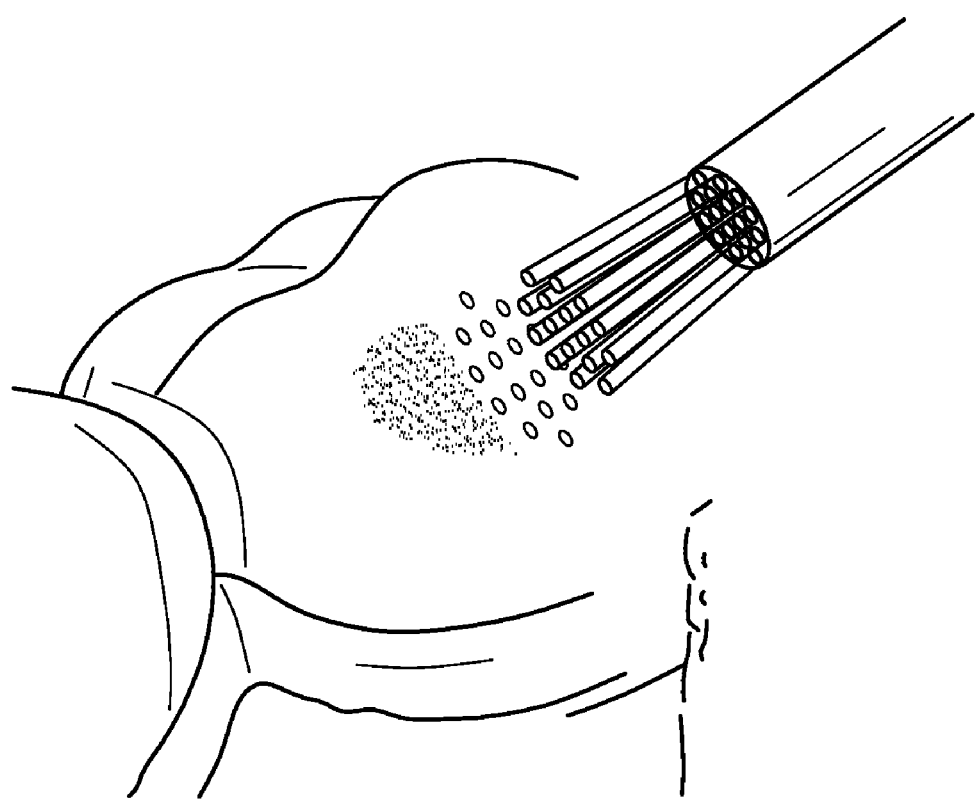
FIGS. 1A-1M are side-elevational and perspective views depicting various features of a first set of embodiments of the present invention.
Figure 1B:
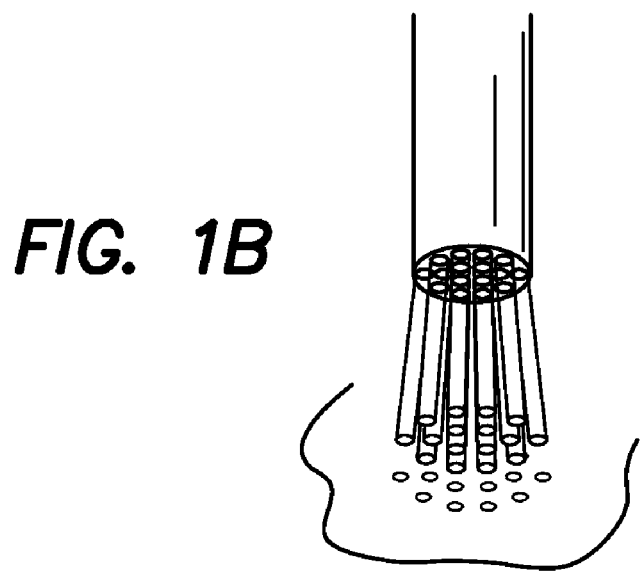

Reference is made to Prov. App. 60/961,113, which contains an article entitled The antimicrobial efficacy of the erbium, chromium:yttrium-scandium-gallium-garnet laser with radial emitting tips on root canal dentin walls infected with *Enterococcus faecalis*. The devices and methods disclosed and referenced herein are intended to relate to and build upon devices and methods disclosed, and referenced, in that article, in part or in whole, in any combination or permutation, with or without modification, as would be understood by one skilled in the art to be possible in view of this disclosure to be feasible or modifiable to be feasible.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not presumed, automatically, to be to precise scale in all embodiments. That is, they are intended to be examples of implementations of various aspects of the present invention and, according to certain but not all embodiments, to be to-scale. While, according to certain implementations, the structures depicted in these figures are to be interpreted to be to scale, in other implementations the same structures should not. In certain aspects of the invention, use of the same reference designator numbers in the drawings and the following description is intended to refer to similar or analogous, but not necessarily the same, components and elements. According to other aspects, use of the same reference designator numbers in these drawings and the following description is intended to be interpreted as referring to the same or substantially the same, and/or functionally the same, components and elements. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent accompanying this disclosure is to discuss exemplary embodiments with the following detailed description being construed to cover all modifications, alternatives, and equivalents of the embodiments as may fall within the spirit and scope of the invention as defined by the appended claims. It is to be understood and appreciated that the process steps and structures described herein do not cover a complete architecture or process, and only so much of the commonly practiced features and steps are included herein as are necessary to provide an understanding of the present invention. The present invention has applicability in the field of laser devices in general. For illustrative purposes, however, the following description pertains to a medical laser device and a method of operating the medical laser device to perform surgical functions.

The invention disclosed and referenced herein relates to electromagnetic energy and/or sound wave emitting devices, such as fiber optic and ultrasonic probes, for treating tissue (e.g., necrotic and/or inflamed tissue) and removing deposits (e.g. plaque and/or calculus) and stains, from surfaces (e.g., hard and soft tissue surfaces). The fiber optic devices and probes may additionally and/or alternatively be used to treat tissues (e.g., hard tissues) and, in certain implementations, to treat surfaces that have lost connective tissue and/or bone responsible for attachment or that have been affected by bacteria, decalcified and/or that require fluoride uptake.

The tissues may comprise, for example, tooth root surfaces, which, for example, may be covered with calculus deposits, plaque and/or various types of stains. Furthermore, the tissues may comprise, for example, surfaces which have been decalcified and/or which require fluoride uptake. Other examples include channels, openings or tissues that have been affected by deposits of plaque, and calcified tissues. The following disclosure elucidates exemplary embodiments that relate to fiber optic and sound emitting probes and devices in accordance with the present invention and that are operative to remove and treat tissue such as surfaces of soft issue, teeth and tooth roots covered by calcified deposits (e.g., calculus) and plaque or various types of stains as well as surfaces that lack attachment or have been decalcified or require fluoride uptake.

The energy source may comprise, for example, (1) a laser with or without a water spray or (2) a laser with or without a water spray in combination with a sonic and/or ultrasonic energy emitting source. In typical embodiments, source specifications may be implemented, as follows: sonic/ultrasonic frequencies or frequency ranges can be within, range, or contain ranges of or within, for example, 10 kHz-50 kHz and 20 kHz-25 kHz; and laser wavelengths or wavelength ranges can be, range, or range within, for example, about 2,789 μm, about 2.94 μm, about 2.69 μm, and/or can be within or range from or within about 2.1 μm to about 3 μm. Fiber lasers can be in the near IR region and Q-switched at kHz frequencies of operation.

Laser wavelengths for photo-biostimulation can take any one or more values or ranges within the following exemplary limits: about 630 nm-700 nm, about 700 nm-850 nm and about 900-980 nm. Photo-biostimulation implementations may include steps and structures, in whole or in part, in any permutation or combination, as will occur, to the extent not mutually exclusive to those skilled in the art upon consideration of the included and referenced disclosures, including those of application Ser. No. 12/204,638, filed on Sep. 4, 2008 and application Ser. No. 11/447,605, filed on Jun. 5, 2006, the entire contents of both which are hereby incorporated by reference.

The laser source or sources can also comprise a wavelength that can be run at KHz frequencies to generate vibrations which may help to dislocate, for example, calcified deposits and/or plaque.

Applications can include removal of calculus deposits, plaque and stains from tooth enamel, tooth root surfaces and tooth cementum; preparation of a smoother enamel or root surface after the removal of calculus deposits; and treatment of a root surface to facilitate precipitation of an amelogenics hydrophobic constituent such as an enamel matrix derivative (e.g., an EMD having a clinical concentration of about 5 mg/ml-50 mg/ml) with or without propylene glycol alginate (PGA). The EMD can be implemented to dissolve in PGA at an acidic pH (with the laser thus being used to dehydrate the tissue surface in order to facilitate deposition of the EMD product). With photo-biostimulation, a source (e.g., a laser or a laser and an ultrasonic source) can be used to induce tissue regeneration for formation of a new attachment comprising new cementum, periodontal ligament (fibroblasts) and/or bone, and to facilitate reduction of bacterial endotoxins.

Energy densities or energy density ranges can be within, contain ranges within, or comprise ranges of about 0.014 $J/cm^2$-250 $J/cm^2$, about 10-50 $J/cm^2$ and/or about 75-120 $J/cm^2$ (e.g., for mid IR laser+water spray implementations). Frequencies of operation for the laser can be or vary between 5-500 Hz or 5-100 Hz, as well as combination frequencies. Pulse durations, having one or more values or ranges from or within 30-300 μs, or combinations of pulses having such durations, may be implemented.

Figure 1C:
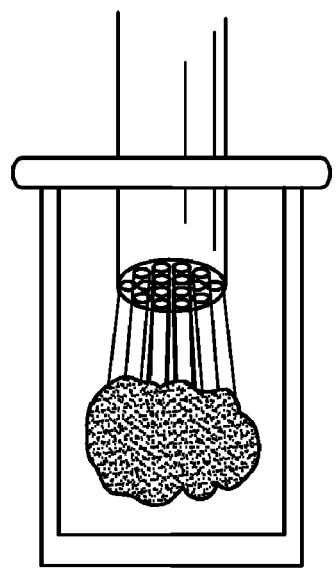
Figure 1D:
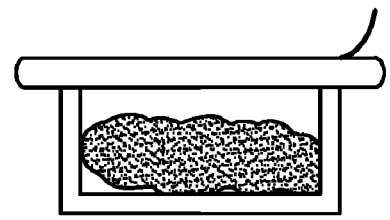
Figure 1F:
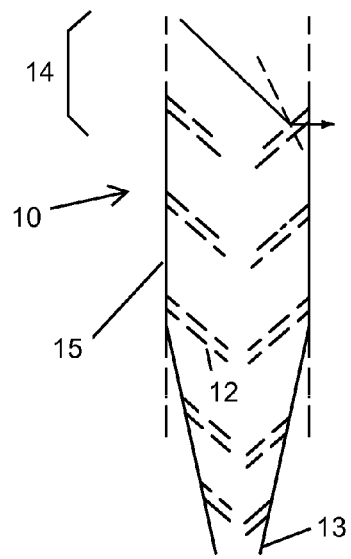
Figure 1G:
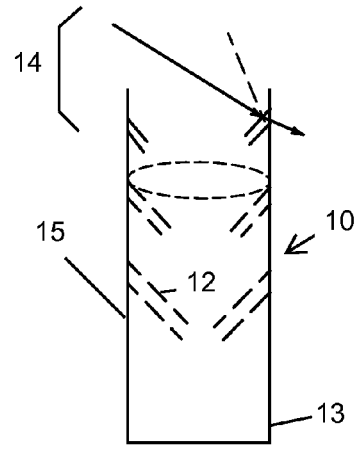
Figure 1H:
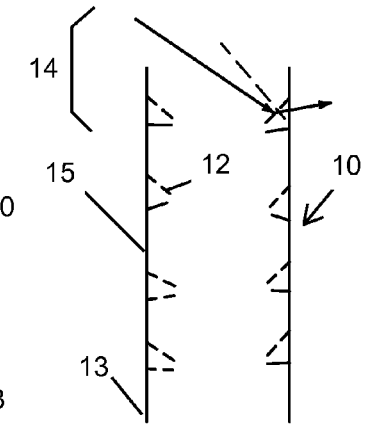
Figure 1I:
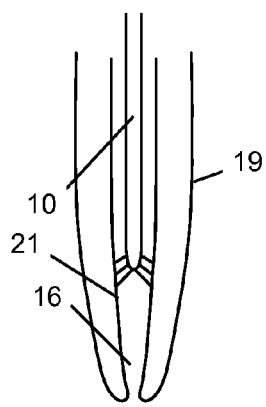
Figure 1J:
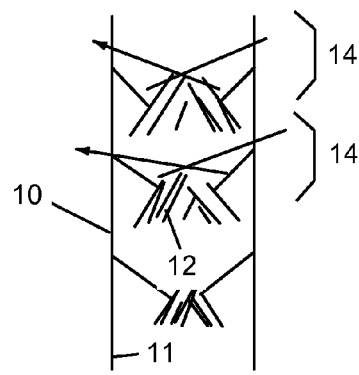
Figure 1K:
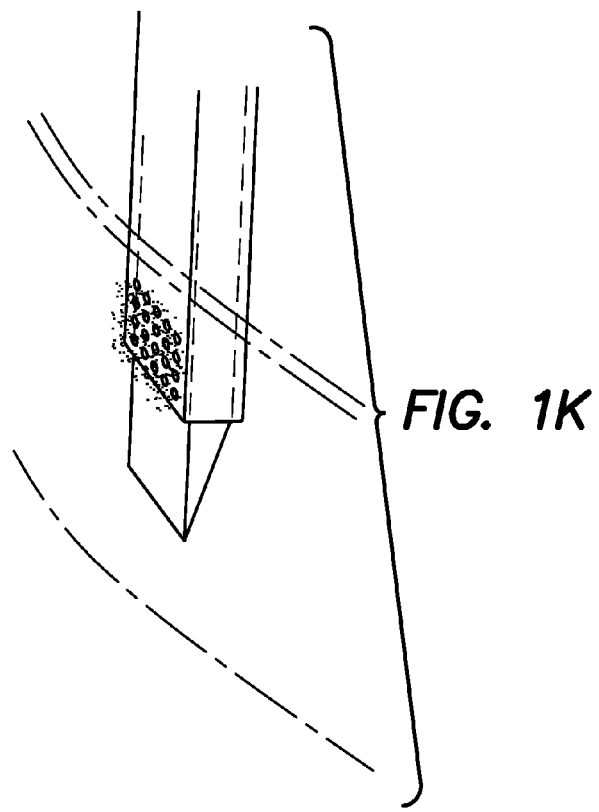
Figure 1L:
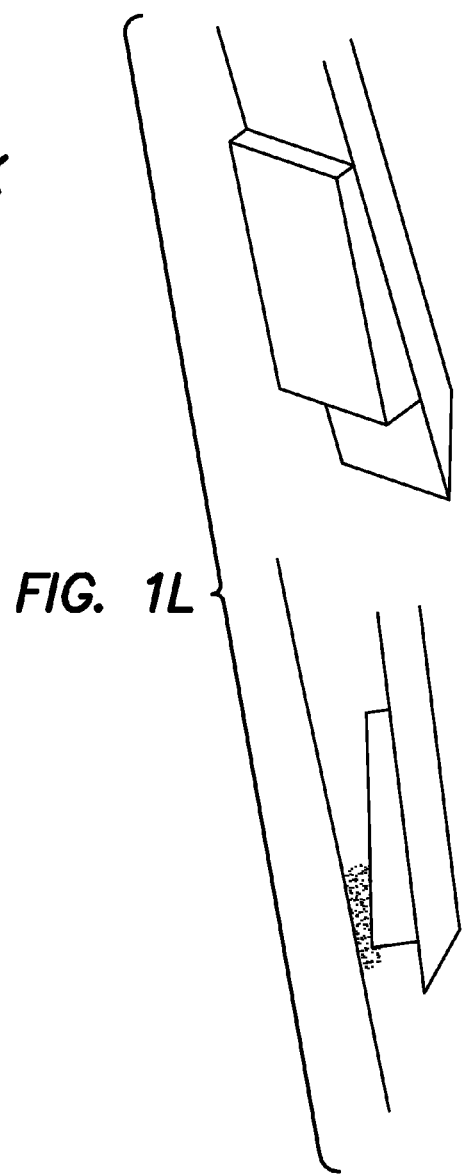
Figure 1M:
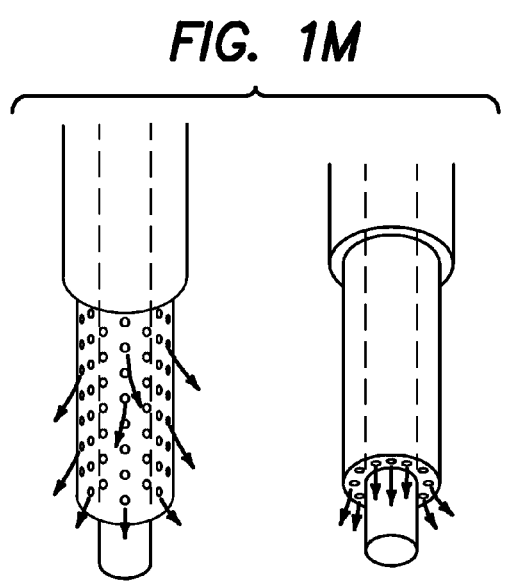
Figure 2A:
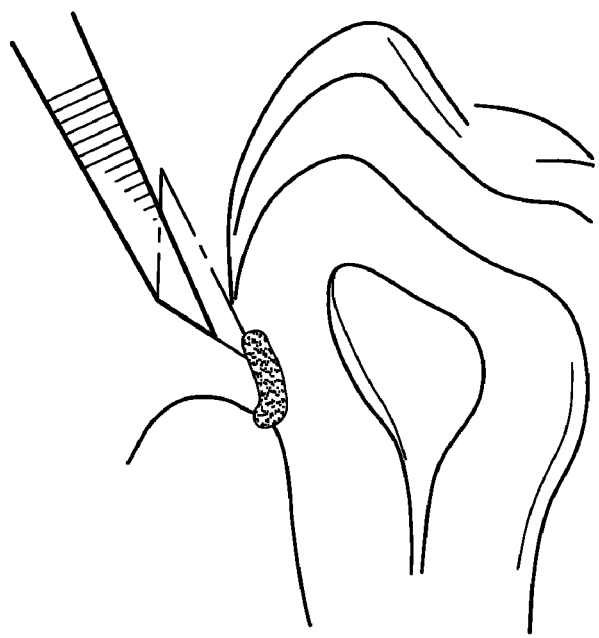
Figure 2B:
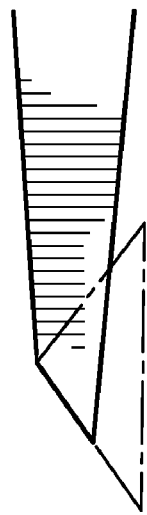

Tips or bundles of tips with or without a dispenser for bio-fluid (e.g. in get and/or liquid form, with different viscosities) may be implemented such as depicted in FIGS. 1K-1M. Exemplary viscosities may range, for example, from about 70,000 centipoise to about 120,000 centipoise. Components or agents of the biofluids, powder, gel or liquid may comprise any part of the items described or referenced in (a) U.S. Pat. No. 5,785,521, and/or (b) document or application that references U.S. Pat. No. 5,785,521.

When a bio-fluid or bio-fluids are implemented, the bio-fluid or bio-fluids may be characterized as follows: the fluid(s) may comprise one or more medicated fluids and/or gels (e.g., EDTA ethylenediaminetetracetic acid (EDTA) 0.01-0.1%, or 0.05%, EMD+PGA 5-50 mg/ml, fluoride (sodium fluoride, etc) X %, potassium nitrate Y %) or an aqueous type fluid that can be used to supplement or replace the water spray.

The currently described embodiments are provided by way of examples, and the present invention is not limited to these examples. Multiple variations and modification to the disclosed embodiments will occur, to the extent not mutually exclusive, to those skilled in the art upon consideration of the included disclosure. Additionally, other combinations, omissions, substitutions and modifications will be apparent to the skilled artisan in view of that described and referenced herein (and/or described or referenced in any of the referenced items).

Any feature or combination of features described and referenced herein (and/or described or referenced in any of the referenced items) are included within the scope of the present invention provided that the features included in any such combination are not mutually inconsistent as will be apparent from the context, this specification, and the knowledge of one of ordinary skill in the art. For example, any of the herein described and/or referenced (e.g., described or referenced herein and/or described or referenced in any of the referenced items) lasers and laser components, including handpiece apparatus (e.g., tips and/or target surface contacting structures and/or methods, and/or items used with, on, inside or in conjunction with the tips and target contacting structures), and any particulars or features thereof, or other features, including method steps and techniques, may be used with any other structure and/or process described or referenced herein (and/or described or referenced in any of the referenced items), whole or in part, in any combination or permutation.

In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. The intent of this disclosure, while discussing exemplary embodiments, is that the included and/or referenced (e.g., described or referenced herein and/or described or referenced in any of the referenced items) structures and/or steps be construed to cover all modifications, alternatives, and equivalents of the embodiments as may fall within the spirit and scope of the invention.

The following illustrations represent conceptual prototypes of sponge/sheath dispensing mechanisms according to the present invention, which mechanisms can be used to hold and position components (e.g., fluids), or components/agents as defined below, in proximity to an output fiber optic tip, or a. probe, for dispensing, for example, of the components (e.g., biofluids or biopowders, as disclosed herein) or components/agents during a procedure such as a treatment procedure on tissue. The sponges and sheaths can be formed, for example, in a compact (e.g., low profile) fashion for providing minimally invasive access to the surgical site of tissue (e.g., a canal, pocket, such as a periodontal pocket, or other formation of tissue).

The sponges can be formed, for example, according to process steps and/or structures as implemented, in whole or in part, in products elucidated and/or referenced in connection with the "K-Sponge" name or brand, such as owned by Katena Products, Inc., of Denville, N.J., the entire set of products and relevant contents of which is incorporated herein by reference.

Components, such as one or more of the fluids, biofluids and biopowders disclosed herein, and/or any sub-components or agents thereof ("components/agents"), may be applied to the sponge in one or more of a powder, liquid and/or intermediate (e.g., gel or part powder/liquid) state, for subsequent release on or near a treatment site. The components/agents may be added in liquid or semi-liquid form before the sponge is formed into a compressed or low-profile shape (using, for example, any one or more parts of the above-referenced K-Sponge technology), followed by, for example, drying (e.g., dehydrating) and compressing of the sponge.

Alternatively, and/or additionally, components/agents may be added in a powder, solid, semi-solid, suspended solid, dissolved or distributed solid, get and/or powder/liquid form before, during and/or after the sponge is formed into a compressed or low-profile shape (using, for example, any one or more parts of the above-referenced K-Sponge technology). In an implementation wherein one or more components/agents are added after the sponge has been formed into a compressed or low-profile shape, the sponge may be contacted with the component(s)/agent(s) by way of (1) dipping of the sponge into a component/agent containing solution, (2) dripping of a liquid containing the component/agent onto the sponge, or touching of the sponge with a powder of or containing the component/agent so that the component/agent attaches to a surface of and/or an interior of the sponge.

The sponges may take various shapes to be effective. These shapes can be, but are not limited to rectangular, point-end, and round-end shapes. Once placed into contact with, for example, fluid in the mouth, the sponge can be configured to expand and allow the release of biofluids or biopowders to the target site to aid the procedure.

The sheaths can be formed, for example, of a silicon type sheet of material. In other embodiments, the sheaths may be formed, in whole or in part, of, for example, gelatin and/or cellulose (e.g., alpha-cellulose). Moreover, the sheaths of the present invention may alternatively or additionally be formed, in whole or in part, of any one or more of the materials, structures, compositions or distributions of compositions, shapes, components/agents and/or steps used to make/use the sponges as described or referenced herein.

The architecture of each sheath may comprise, for example: (a) a construction with one or more pores or perforations disposed anywhere along a length thereof and/or (b) a construction without pores and an opening at a distal end thereof. Either or both of the (a) and (b) constructions can be configured for dispensing the components/agents (e.g., biofluids, biopowders and/or other material) as, for example, described and depicted herein. Once pressed into contact with, for example, tissue, the sheath may release biofluids or biopowders to the target site to aid the procedure.

Furthermore, components/agents may be disposed (e.g., selectively disposed) on or in only parts of the sponge or sheath, such as on and/or in one or more of: selected (e.g., partial) area(s), selected volume(s), a single side, selected pores, other surface features or indentations, all pores or other surface features or indentations, and combinations thereof.

Combination embodiments comprising hybrid sponge/sheath implementations, such as a sheath made of a sponge-like material, may also be implemented. As another example of a modification, rather than or in addition to a sponge or a sheath of sponge-like material, and/or in any embodiment described herein, an external surface of the sponge and/or sheath can be formed with surface irregularities (e.g., features) to hold components/agents (e.g., biofluids or biopowders), such as, for example, bristles. Another application for the same sponge and/or sheath (without biofluids or biopowders) is the use of removing material from the tissue site. The sponge and/or sheath can absorb and collect dislodged materials (e.g., calculus deposits and/or removed tissue, dislodged or removed by way of, for example, the probe, fiber, other implement to which the sponge is affixed) from the site instead of using suction or other methods of removing the debris from the target.

Any of the implementations described or referenced herein may be loaded with a component/agent (e.g., biofluid or biopowder) that, for example, (1) softens a component or agent on a surface of the target (e.g., a calculus deposit, and/or with such softening agent being, e.g., propylene glycol alginate (PGA)—whereby, for example, EMD dissolves in PGA at acidic pH (and/or, for example, a laser may be used to dehydrate tissue surface in order to facilitate the deposition of the EMD product)); (2) cleans the target (e.g., root) surface (e.g., an acidic component and/or etching agent, e.g., EDTA); and/or (3) medicaments such as anesthetizing agents, growth promoters, etc.

With reference to FIGS. 1A-1J, side-elevational and perspective views depict various features of a first set of embodiments of the present invention in the context of laser-assisted stain and/or plaque removal. As can be discerned from FIGS. 1A and 1B, a main fiber houses a plurality of optical fibers which may take the form of individual, non-connected optical fibers or may take the form, in whole or in part, of a fiber bundle fused into the main fiber. In either configuration, the optical fibers exit out of and extend from a distal end of the main fiber. Side-firing fiber optic tips are shown in FIGS. 1F-1H, with FIG. 1I depicting a side-firing fiber optic tip disposed within a root canal of a tooth and FIG. 1J providing a cross-sectional view, with beam traces, of a side-firing fiber optic tip. The optical fibers may comprise or function as bristles (e.g., soft or hard cleaning bristles) having diameters of, for example, about 50 µm to about 300 µm. A dentifrice (e.g., a gel or paste), such as shown in FIGS. 1C and 1D, may be provided in a cartridge whereby the configuration comprises dentifrice disposed either preloaded on the optical fibers (FIG. 1C) in the form of a preloaded tip package or by itself (FIG. 1D) in the form of a refill package.

FIGS. 2A-2E are side-elevational and perspective views of various features of a second set of embodiments of the present invention. The device shown in the side-elevational and perspective views corresponds to an embodiment of the present invention that is operational as a laser scalpel for calculus removal. As can be discerned from FIGS. 2A and 2B, the laser scalpel outputs laser light according to, for instance, an output format taking the shape of a triangularly-shaped beam trace.

Figure 2C:
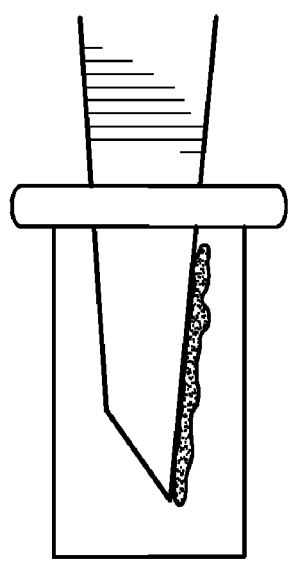
FIGS. 2A-2E are side-elevational and perspective views of various features of a second set of embodiments of the present invention.
Figure 2D:
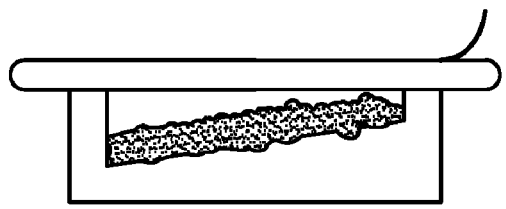
Figure 1E:
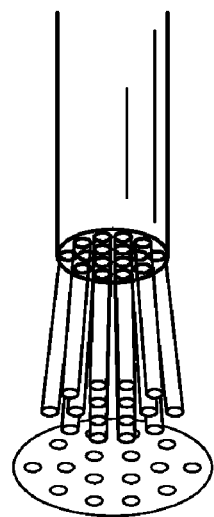
Figure 2E:
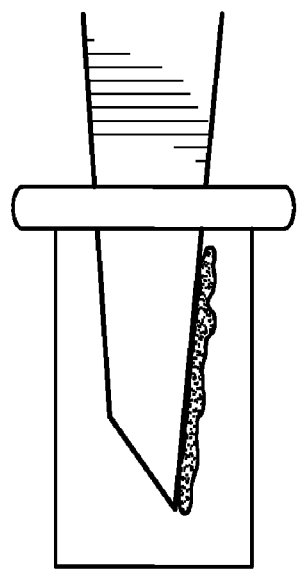

A dentifrice (e.g., a gel or paste), such as shown in FIGS. 2C and 2D, may be provided in a cartridge either preloaded on the laser scalpel (FIG. 2C) to form a preloaded tip package or by itself (FIG. 2D) to form of a refill package. As represented in FIG. 2E, the dentifrice can be disposed over the output surface of the laser scalpel at a thickness ranging from about 50 µm to about 1000 µm or, in certain embodiments at a thickness of about 50 µm to about 500 µm, or in other embodiments at a thickness of about 50 µm to about 250 µm. A peel-off seal can be provided over the dentifrice and/or over a side of the cartridge.

With reference to FIGS. 1A-1J, other embodiments can be fiber bundles with non cylindrical (e.g., non truncated) distal ends (e.g., angled, beveled, double-beveled, etc. distal ends) to provide different energy outputs with varying characteristics. For such bundled embodiments one or more components/agents (e.g., a viscous component(s)) may be disposed in one or more of a central area or lumen and a peripheral area(s) of the optical fibers, and/or may be disposed or dispersed between two or more of the optical fibers. While the cross-section of one or more of FIGS. 1A-1E shows a circular cross-sectional area wherein the body of each fiber bundle resembles an envelope (i.e., shape) of a cylinder, other cross-sectional shapes are also possible, such as rectangular shape or other shapes.

In other embodiments, the cross-sections may correspond to flat or blade configurations of fiber bundles. Thus, as an example of a "thin blade" fiber bundle configuration, a cross section may comprise a single, straight (or, alternatively, arched) row formed by five circles (i.e., "ooooo") corresponding to a fiber bundle formed of five fiber optics and having a flat (or, alternatively, arched) cross-sectional shape (rather than the illustrated circular cross-sectional shape). As another example, which may be used as an alternative to the mentioned "thin blade" fiber bundle, a "double-thickness blade" construction may include a fiber bundle configuration, a cross section of which comprises a single, straight (or, alternatively, arched) row formed by two rows of five circles (i.e., "ooooo") each corresponding to a fiber bundle formed to be five fiber optics wide and two fiber optics thick and having a flat (or, alternatively, arched) cross-sectional shape (rather than the illustrated circular cross-sectional shape). As another example, a "triple-thickness blade" construction may include a fiber bundle configuration, a cross section of which comprises a single, straight (or, alternatively, arched) row formed by three rows of five circles (i.e., "ooooo") each corresponding to a fiber bundle formed to be five fiber optics wide and three fiber optics thick and having a flat (or, alternatively, arched) cross-sectional shape.

FIGS. 3A-3D provide plan and cross-sectional views of sponges, sheaths, cannulas, and optical fiber tips (e.g., of sapphire) in accordance with implementations of the present invention. Regarding the discussion concerning modifications of the preceding paragraphs, rather than the number of "five" (or other number of) fiber optics, other implementations may comprise other numbers such as ten, fifteen, twenty, or more fiber optics, Additionally, as another alternative to the number of "five" (or other number of) fiber optics, other implementations may comprise a continuous compartment such as that symbolized, for example, by "====" (c.f., FIG. 3A) rather than "ooooo" (e.g., the equivalent of an infinite number of fiber optics, or an interior formed between two planar, e.g., straight or arched, surfaces). The light transmitting centers or compartments (e.g., of the fiber optic or continuous compartment) may be hollow or solid, and may be bordered by one or more of a skin, jacket or outer wall (e.g., reflective or, alternatively, transmissive to a wavelength or the wavelength of radiation).

Figure 3A:
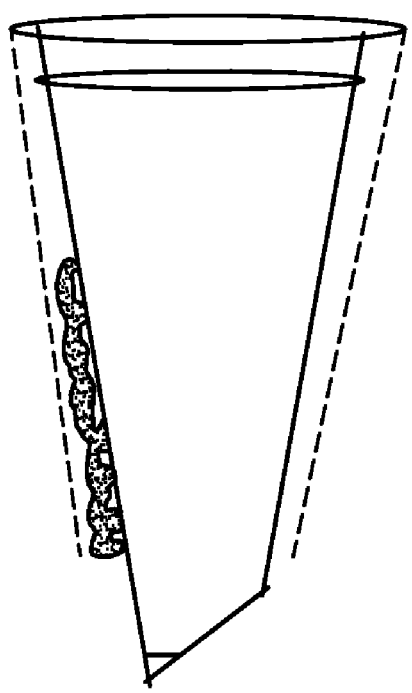
FIGS. 3A-3D provides cross-sectional views of sponges, sheaths, cannulas, and tips in accordance with implementations of the present invention.
Figure 3B:
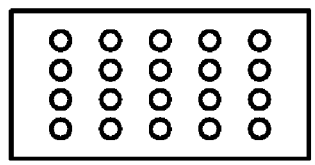
Figures 3C, 3D:
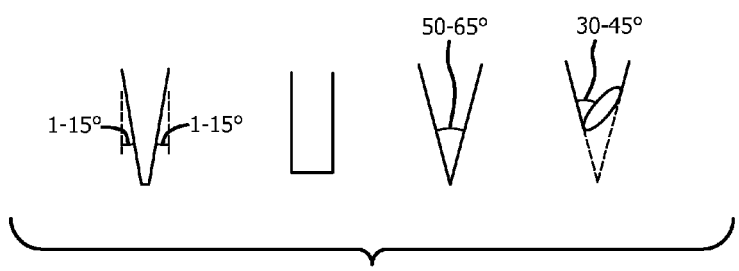
Figure 4A:
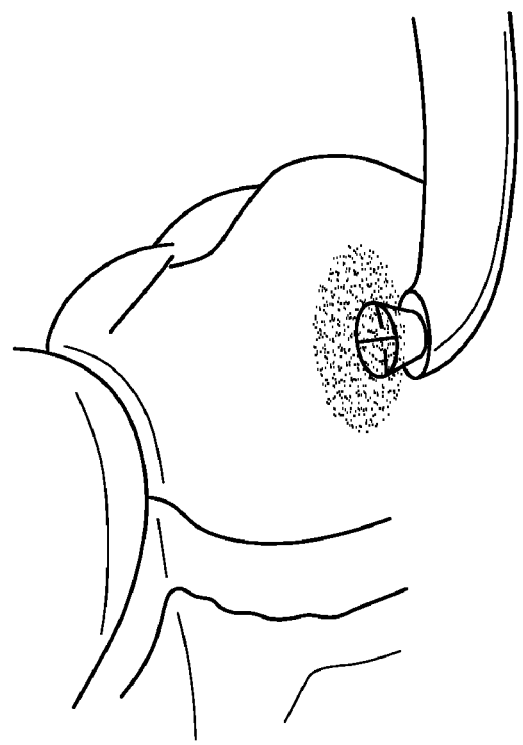
FIGS. 4A-4D depict disposable prophy angle implementations in accordance with the present invention, in which a light source is located within (e.g., centrally within) the flexible cup.
Figure 4B:
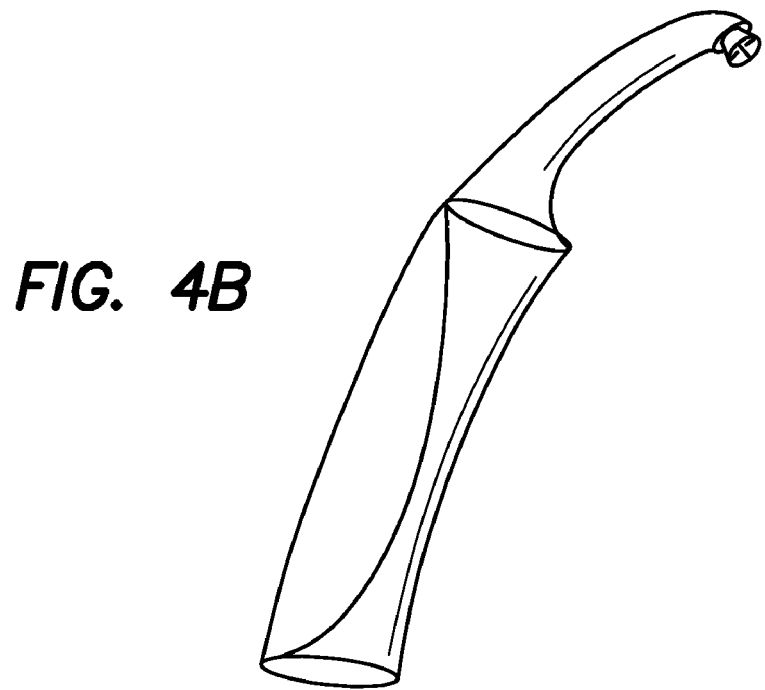
Figure 4C:
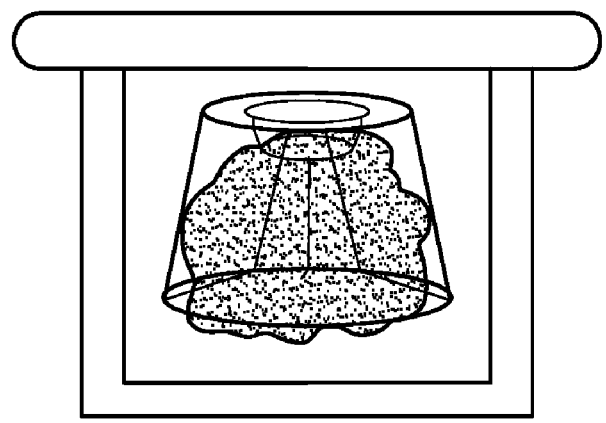

In still other embodiments, the cross-sections may correspond to oval or circular (e.g., with cross-sectional areas that do not change in the distal direction, or that decrease in the distal direction such as in FIGS. 3A, 3C and 3D, or that increase in the distal direction such as in FIGS. 4A, 4B and 4C) configurations of fiber bundles. As an example, a cross section may comprise a single, closed row formed by about six circles (i.e., "oooooo") corresponding to a fiber bundle formed of six fiber optics and having an oval or circular cross-sectional shape. Other examples may comprise any fewer or, typically, greater number of circles, such as ten, twenty, or more. Other examples, which may be used as an alternative to any mentioned single-row implementation of an oval or circular shape, can comprise, for example, a double-row or triple-row of fiber optics ("oooooo") each corresponding to a fiber bundle formed to be six fiber optics wide and two, or three, fiber optics thick.

Additionally, as an alternative to the mentioned "six" (or other number of) fiber optics, other implementations may comprise a continuous compartment such as that symbolized, for example, by "====" rather than "oooooo" (e.g., the equivalent of an infinite number of fiber optics, or an interior formed between two planar, e.g., straight or arched, surfaces). The light transmitting centers or compartments (e.g., of the fiber optic or continuous compartment) may be hollow or solid, and may be bordered by one or more of a skin, jacket or outer wall (e.g., reflective or, alternatively, transmissive to a wavelength or the wavelength of radiation). For instance, the structure defining the prophy cup of FIG. 4A may be transparent to a wavelength(s) of radiation (e.g., laser or LLLT energy) emitted from the device. The light transmitting centers or compartments may be hollow or solid.

The skin, jacket or outer wall, which may border the light transmitting center or compartment (e.g., of the fiber optic or continuous compartment), according to certain embodiments such as shown in FIG. 3A, may be porous. In other implementations, such as exemplified in FIGS. 4A to 4C, the skin, jacket or outer wall may be nonporous. According to typical implementations, the skin, jacket or outer wall may comprise a porous construction as elucidated in FIG. 3B and/or may comprise (e.g., consist of) a sponge or sheath as described herein. In one implementation, the light-transmitting center is bordered with a sponge or sheath (e.g., a wall or a membrane that is: flexible, rigid, fabric, removable, permanently attached, porous, perforated e.g. as in FIG. 3B, nonporous, nonperforated, and/or of the same or different material as the tip) over one of its two planar/arched boundaries.

Figure 3E:
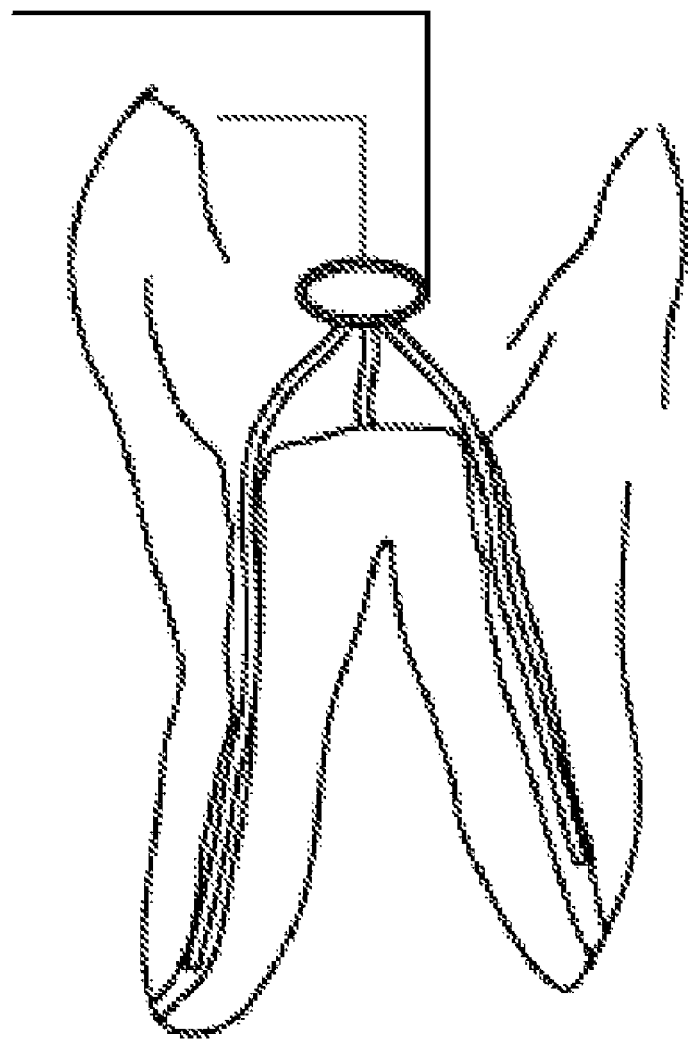
FIG. 3E depicts side-firing fiber optics and their fiber optic tips extending from a handpiece and branching into root canals of a tooth.

In another implementation, the light-transmitting center is bordered with a sponge or sheath (e.g., a wall or a membrane that is: flexible, rigid, fabric, removable, permanently attached, porous, perforated e.g. as in FIG. 3B, nonporous, nonperforated, and/or of the same or different material as the tip) over both of its planar/arched boundaries. In yet another implementation, all or substantially all of the light-transmitting center is surrounded with sponge or sheath (e.g., a wall or membrane that is: flexible, rigid, fabric, removable, permanently attached, porous, perforated e.g. as in FIG. 3B, nonporous, nonperforated, and/or of the same or different material as the tip). The wall(s) or membrane(s) may correspond to a shape encompassing part or all of any fiber optic described or referenced herein (e.g., cf. FIGS. 3A-3D). FIG. 3E depicts side-firing fiber optics, embodied as multi-fiber optics, or, alternatively, single fiber optics, extending from a handpiece and branching into one or more root canals and/or dentinal tubules, of a tooth.

Furthermore, the wall(s) membrane(s) may comprise, take the form, resemble, or serve as a prophy cup as depicted in FIGS. 4A-4D. With more particular reference to such constructions, FIGS. 4A-4D depict disposable prophy angle implementations in accordance with the present invention, in which a light source is located within (e.g., centrally within) the head of the device, for facilitating, according to typical uses, one or more of laser polishing and laser or light assisted brightening of a tooth surface. In a typical implementation, a light source(s) is disposed to emit light from within (e.g., centrally within) the prophy cup (e.g., flexible prophy cup) in a direction out of and/or distally away from the prophy cup.

Typical uses of the depicted prophy angle implementations may function to achieve polishing and/or brightening, by operation of (a) emission of light from the light source within and/or from the prophy cup in combination with (b) a mechanical operation (e.g., mechanized, repeating movement) of the prophy cup (e.g., the light-transmitting prophy cup). In addition to emitting light (e.g., laser light), the head can be enabled/provided and used with one or more automated (e.g., electrically-powered) mechanical capabilities/operations as are known in the art for construction and operation of prophy cup dental devices.

Figure 4D:
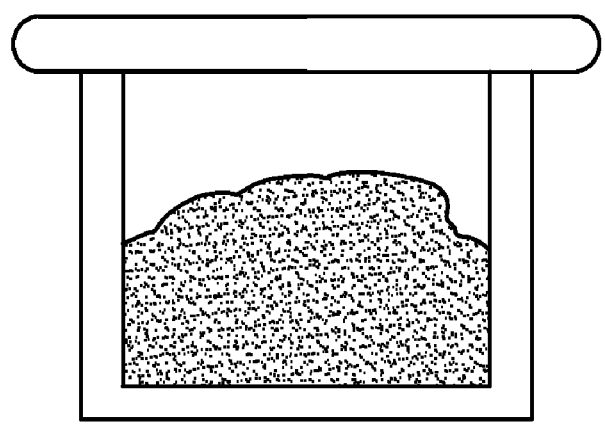

A dentifrice (e.g., a gel or paste) such as shown in FIGS. 4C and 4D can be provided in a cartridge, either preloaded on the prophy cup (FIG. 4C) in the form of a preloaded cup package, or by itself (FIG. 4D) in the form of a refill package. A peel-off seal can be provided over the dentifrice and/or over a side of the cartridge.

Additionally, any of the compartments may comprise structure for carrying any type of fluid described or referenced herein as an alternative to or in addition to a gel or paste as embodied, for example, in connection with the dispensing cannula of FIGS. 3A and 3B. The dispensing cannula of FIG. 3A can encompass, embody, or be defined by, one or more of the above mentioned sponges or sheaths, so that, for example, the interior of the cannula may correspond to the above mentioned transmitting centers or compartments.

A typical dispensing cannula may be formed, for example, of one or more of a silicon type material and a material in the form of a relatively soft membrane. A permeability, if any, of the dispensing cannula can be engineered to vary according to the number of emitting channels/perforations, to thereby control a degree or rate of dispensing of a gel or paste. According to contemplated configurations having permeabilities, channels, pores, or perforations of the dispensing cannula may have diameters ranging from about 50 μm to about 500 microns, and center-to-center gaps with dimensions ranging from about 250 μm to about 550 microns.

In the particular construction exemplified in FIG. 3A, the dispensing cannula may extend close to but not all of the way to or over, the distal tip. Typical implementations can comprise the dispensing cannula not extending over the final (i.e., distal) 1 to 3 mm of the optical fiber as shown. According to other implementations in which, for example, the dispensing cannula does not cover the final 1 to 3 mm of the optical fiber, this uncovered portion may be coated, in whole or in part, with a dentifrice such as a gel.

Optical fiber characteristics (e.g., dimensions), which may be varied to control operability, such as a treatment characteristic and/or a rate of dispensing of a gel or paste, can include one or more of tip geometry, length, cross-sectional length, cross-sectional width, and power density. As an example, the construction in FIG. 3A can have a pointed distal tip or a truncated (e.g., flat) distal tip. A construction with a truncated distal tip, as shown, may comprise, for example, a flat distal end with a diameter ranging from about 50 μm to about 200 μm to facilitate, for example, light leakage.

As elucidated by the exemplary depictions in FIG. 3D, constructions of the distal end of an optical fiber(s) can have sides which taper in a distal direction, whereby such tapering sides may have angles of about 1 to about 15 degrees relative to a longitudinal axis of the optical fiber. The angles of adjacent, opposing, or otherwise disposed, tapering side(s) of an optical fiber may or may not be symmetrical with respect to one or more of each other and the longitudinal axis of the optical fiber. Thus, for example, an optical fiber tip may be formed with two opposing sides having different taper angles so that the two sides are asymmetrical with respect to both one another and the longitudinal axis of the optical fiber.

As with the construction of FIG. 3A, distal tips of any of the optical fiber tips depicted in FIG. 3D, or other figures, can have a truncated (e.g., flat) distal tip which may be oriented normal to the longitudinal axis of the optical fiber, or not, which may be planar (e.g., flat), or not (e.g., curved), and/or which may be circular, or not (e.g., oval). Furthermore, the structures of FIGS. 3A and 3B, and the structures of FIGS. 3C and 3D, in any number, permutation, or combination, can be interpreted, or formed, as or in combination with, in whole or in part, any one or more of the herein described or referenced optics, tips, fibers, fiber optics, fiber bundles; and/or may have in whole or in part any of the described transmitting centers, compartments, skins, jackets, outer walls, sponges, sheaths or dispensing cannulas.

Any one or more of the herein described or referenced optics, tips, fibers, fiber optics, and/or fiber bundles may comprise shapes, surfaces, structures and/or functions as described or referenced in one or more of the documents referenced herein, including, application Ser. No. 11/033,043 filed Jan. 10, 2005; application Ser. No. 09/714,497 filed Nov. 15, 2000; application Ser. No. 11/800,184, Int. App. PCT/US08/52106; and application Ser. No. 11/033,441.

Lumens of any of the structures herein described or referenced may be provided with any one or more of the structures and/or arrangements as disclosed, referenced, or taught by any one or more of the documents referenced herein, including, application Ser. No. 11/033,043 filed Jan. 10, 2005; application Ser. No. 09/714,497 filed Nov. 15, 2000; application Ser. No. 11/800,184, Int. App. PCT/US08/52106; and application Ser. No. 11/033,441. For instance, the area inside of the prophy cup of FIG. 4A may correspond to the distal end of, for example, any of FIGS. 9b, 10b, 11b or 11c of application Ser. No. 11/033,043; or the area inside of the prophy cup of FIG. 4A may correspond to the distal end of, for example, any of FIG. 4 or 5 of U.S. Pat. No. 5,741,247.

Furthermore, any embodiment described or referenced may comprise one or more of the fiber optics (e.g., of a give fiber bundle) having a shape other than that of a regular, conventional, cylindrically-shaped fiber optic end (i.e., a truncated fiber end corresponding or identical to the shape of a cylinder). For example, one or more of the fiber optics may comprise a planar, beveled output end of any orientation and/or may comprise an output end that may be wholly or partially spherical, rounded, jagged, chiseled or otherwise shaped for altering a light-intensity output distribution thereof, as compared to a truncated fiber end.

Use of side-firing tips can increase the probability that the emitted laser radiation will enter dentinal tubules and have an effect on bacteria (e.g., to attenuate or eliminate endodontic infection) that are some distance from the canal. Distal ends or regions of the fiber output tips (e.g., side-firing tips and/or tips formed of sapphire or quartz) can be formed with jackets or without jackets such as disclosed, for example, in the herein referenced patents and patent applications.

In another implementation, a user can dip the fiber or bundled fiber construction into a component or medicament (e.g., any biofluid or biopowder as described herein), before use thereof. Any of such constructions may be implemented as a single fiber, as well, as distinguished from a fiber bundle. Also, the "sheath" may be embodied, in addition and/or as an alternative to any of the implementations described herein, as a side cannula as elucidated in the bottom center cross-sectional schematic provided in one or more of FIGS. 4C and 4D (e.g., for holding/dispensing components (e.g., biofluids biopowders) along length thereof); thus, a single or an additional cannula or cannulas can be provided on the side each with a single output at its distal end and/or with one or more output apertures along a length thereof, alone or in addition to, for example, a central cannula-type (e.g., lumen) structure for holding/dispensing components (e.g., biofluids or biopowders) along length thereof.

According to certain implementations, laser radiation is output from a power or treatment fiber (e.g., forming or within a probe), and is directed, for example, into fluid (e.g., an air and/or water spray or an atomized distribution of fluid particles from a water connection and/or a spray connection near an output end of the handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, application Ser. No. 11/042,824 and Prov. App. 60/601,415. The power or treatment fiber may be coupled to an electromagnetic radiation source comprising, for example, one or more of a wavelength within a range from about 2.69 to about 2.80 μm and a wavelength of about 2.94 microns. In certain implementations the power fiber may be coupled to one or more of a diode, an Er:YAG laser, Er:YSGG laser, an Er, Cr:YSGG laser and a CTE:YAG laser, and in particular instances may be coupled to one of an Er, Cr:YSGG solid state laser having a wavelength of about 2.789 μm and an Er:YAG solid state laser having a wavelength of about 2.940 microns. An apparatus including corresponding structure for directing electromagnetic radiation into an atomized distribution of fluid particles above a target surface is disclosed, for example, in the below-referenced U.S. Pat. No. 5,741,247, which describes the impartation. of laser radiation into fluid particles to thereby apply disruptive forces to the target surface.

According to exemplary embodiments, operation in one or more of a gaseous and a liquid environment (e.g., within a channel or canal) can comprise a laser (e.g., an Er, Cr:YSGG solid state laser) having: a repetition rate of about 10 or 20 Hz or, in other implementations (e.g., for one or more of a relatively larger channel and a more calcified or stubborn target) about 30 to 50 Hz; and an energy per pulse from about 2 to 60 mJ, or in other embodiments (e.g., for one or more of a relatively larger channel and a more calcified or stubborn target) greater than 60 mJ such as levels up to about 150 mJ or 200 mJ. The higher frequencies are believed potentially to enhance an efficiency or efficacy of one or more of enlargement and shaping, root canal debridement and cleaning, pulp extirpation, pulpotomy for root canal therapy, sulcular debridement, and others. For exemplary channel transverse-widths (e.g., diameters) greater than 25 microns, such as those ranging from about 250 to 450, or 600, microns, probe or fiber diameters may range from about 10 to 450 microns, or from about 25 to 300 microns.

For channels comprising one or more of a relatively large diameter (e.g., about 400 or 450 to about 600, or more, microns) and a more calcified or stubborn target, probe or fiber diameters may range from about 300 to 400, or 500, or 600, or more, microns. An example may comprise a 200 to 300 μm fiber, outputting radiation at about 60 mJ/pulse and 50 Hz, in a 250 to 600 μm wide canal. Probe or fiber output regions may comprise, for example, one or more of the structures and functions as disclosed in, for example, any of Prov. App. 61/012,446, Prov. App. 60/995,759, Prov. App. 60/961,113, application Ser. No. 11/800,184, Int. App. PCT/US08/521106, application Ser. No. 11/330,388, application Ser. No. 11/033,441, and U.S. Pat. No. 7,270,657. As an example, the outputting distal end of a probe or fiber may comprise a conical shape having a full angle of about 45 to 60 degrees and/or may comprise one or more beveled surfaces.

The discussion and illustrations of Prov. App. 60/995,759 represent conceptual prototypes of sponge/sheath dispensing mechanisms according to the present invention, which mechanisms can be used to hold and position components (e.g., fluids), or components/agents/particles, in proximity to a probe or output fiber optic tip, for dispensing, for example, of the components (e.g., biofluids, particles and/or biopowders, as disclosed herein) or components/agents during a procedure such as a treatment procedure, mode, or sub-procedure on tissue (e.g., within a canal). The sponges and sheaths can be formed, for example, in a compact (e.g., low profile) fashion for providing minimally invasive access to the surgical site of tissue (e.g., a canal, pocket, such as a periodontal pocket, or other formation of tissue).

The sponges can be formed, for example, according to process steps and/or structures as implemented, in whole or in part, in products elucidated and/or referenced pertaining to "K-Sponges." Components, such as one or more of fluids, biofluids and biopowders (e.g., particles), and/or any subcomponents or agents thereof ("components/agents"), may be applied to the sponge in one or more of a powder, liquid and/or intermediate (e.g., gel or part powder/liquid) state, for subsequent release on or near a treatment site. The components/agents may be added in liquid or semi-liquid form before the sponge is formed into a compressed or low-profile shape (using, for example, any one or more parts of K-Sponge technology), followed by, for example, drying (e.g., dehydrating) and compressing of the sponge. Alternatively, and/or additionally, components/agents may be added in a powder, solid, semi-solid, suspended solid, dissolved or distributed solid, gel and/or powder/liquid form before, during and/or after the sponge is formed into a compressed or low-profile shape (using, for example, any one or more parts of K-Sponge technology).

In an implementation wherein one or more components/agents are added after the sponge has been formed into a compressed or low-profile shape, the sponge may be contacted with the component(s)/agent(s) by way of (1) dipping of the sponge into a component/agent containing solution, (2) dripping of a liquid containing the component/agent onto the sponge, or touching of the sponge with a powder of or containing the component/agent so that the component/agent attaches to a surface of and/or an interior of the sponge. The sponges may take various shapes to be effective. These shapes can be, but are not limited to rectangular, point-end, and round-end shapes. Once placed into contact with, for example, fluid in the mouth, the sponge can be configured to expand and allow the release of biofluids or biopowders particles) to the target site to aid the procedure.

The sheaths can be formed, for example, of a silicon type sheet of material. In other embodiments, the sheaths may be formed, in whole or in part, of, for example, gelatin and/or cellulose (e.g., alpha-cellulose). Moreover, the sheaths of the present invention may alternatively or additionally be formed, in whole or in part, of any one or more of the materials, structures, compositions or distributions of compositions, shapes, components/agents and/or steps used to make/use the sponges. The architecture of each sheath may comprise, for example: (a) a construction with one or more pores or perforations disposed anywhere along a length thereof and/or (b) a construction without pores and an opening at a distal end thereof Either or both of the (a) and (b) constructions can be configured for dispensing the components/agents (e.g., biofluids, biopowders, particles and/or other material) as, for example, described and depicted. Once pressed into contact with, for example, tissue, the sheath may release biofluids or biopowders (e.g., particles) to the target site to aid the procedure. Furthermore, components/agents may be disposed (e.g., selectively disposed) on or in only parts of the sponge or sheath, such as on and/or in one or more of: selected (e.g., partial) area(s), selected volume(s), a single side, selected pores, other surface features or indentations, all pores or other surface features or indentations, and combinations thereof.

Combination embodiments comprising hybrid sponge/sheath implementations, such as a sheath made of a sponge-like material, may also be implemented. As another example of a modification, rather than or in addition to a sponge or a sheath of sponge-like material, and/or in any embodiment described, an external surface of the sponge and/or sheath can be formed with surface irregularities (e.g., features) to hold components/agents (e.g., biofluids or biopowders (e.g., particles)), such as, for example, bristles. Another application for the same sponge and/or sheath (without biofluids, particles, or biopowders) is the use of removing material from the tissue site. The sponge and/or sheath can absorb and collect dislodged materials (e.g., calculus deposits and/or removed tissue, dislodged or removed by way of, for example, the probe, fiber, other implement to which the sponge is affixed) from the site instead of using suction or other methods of removing the debris from the target.

Any of the implementations described or referenced herein may be loaded with a component/agent (e.g., biofluids, particles or biopowders) that, for example, (1) softens a component or agent on a surface of the target (e.g., a calculus deposit, and/or with such softening agent being, e.g., propylene glycol alginate (PGA)—whereby, for example, EMD dissolves in PGA at acidic pH (and/or, for example, a laser may be used to dehydrate tissue surface in order to facilitate the deposition of the EMD product)); (2) cleans the target (e.g., root) surface (e.g., an acidic component and/or etching agent, e.g., EDTA); and/or (3) medicaments such as anesthetizing agents, growth promoters, etc.

With reference to the last sheet of the drawings of Prov. App. 60/995,759, other embodiments can be fiber bundles with non cylindrical (e.g., non truncated) distal ends (e.g., angled, beveled, double-beveled, etc. distal ends) to provide different radiation outputs with varying characteristics. For such bundled embodiments one or more components/agents (e.g., a viscous component(s)) may be disposed in one or more of a central area or lumen and a peripheral area(s) of the fiber optic tip fibers, and/or may be disposed or dispersed between two or more of the fiber optic tip fibers. While the cross-section at the top of this last sheet of drawings shows a circular cross-sectional area wherein the body of each fiber bundle resemble an envelope (i.e., shape) of a cylinder, other cross-sectional shapes are also possible, such as rectangular shape or other shapes. In other embodiments, the cross-sections may correspond to flat or blade configurations of fiber bundles. Thus, as an example of a "thin blade" fiber bundle configuration, a cross section may comprise a single, straight line formed by five circles (i.e., "ooooo") corresponding to a fiber bundle formed of five fiber optic tips and having a flat cross-sectional shape (rather than the illustrated circular cross-sectional shape). As another example, which may be used as an alternative to the mentioned "thin blade" fiber bundle, a "double-thickness blade" construction may include a fiber bundle configuration, a cross section of which comprises a single, straight line formed by two rows of five circles (i.e., "ooooo") each corresponding to a fiber bundle formed to be five fiber optic tips wide and two fiber optic tips thick and having a flat cross-sectional shape (rather than the illustrated circular cross-sectional shape). Furthermore, any embodiment described or referenced may comprise one or more of the fiber optic tips (e.g., of a given fiber bundle) having a shape other than that of a regular, conventional, cylindrically-shaped fiber optic tip end (i.e., a truncated fiber end corresponding or identical to the shape of a cylinder). For example, one or more of the fiber optic tips may comprise a planar, beveled output end of any orientation and/or may comprise an output end that may be wholly or partially spherical, rounded, jagged, chiseled or otherwise shaped for altering a light-intensity output distribution thereof, as compared to a truncated fiber end.

In another implementation, a user could dip the fiber or bundled fiber construction into a component or medicament (e.g., any biofluids, particles or biopowders as described herein), before use thereof. Any of such constructions may be implemented as a single fiber, as well, as distinguished from a fiber bundle. Also, the "sheath" may be embodied, in addition and/or as an alternative to any of the implementations described herein, as a side cannula as elucidated in the bottom center cross-sectional schematic provided on the last sheet of drawings (e.g., for holding/dispensing components (e.g., biofluids, biopowders or particles) along length thereof); thus, a single or an additional cannula or cannulas can be provided on the side each with a single output at its distal end and/or with one or more output apertures along a length thereof, alone or in addition to, for example, a central cannula-type (e.g., lumen) structure for holding/dispensing components (e.g., biofluids, biopowders or particles) along length thereof.

By way of the disclosure herein, a laser has been described that can output electromagnetic radiation useful to diagnose, monitor and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for illumination and/or diagnostics may be transmitted simultaneously with, or intermittently with or separate from, transmission of the treatment radiation and/or of the fluid from the fluid output or outputs.

Corresponding or related structure and methods described in the following patents assigned to BIOLASE Technology, Inc., are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part(s) of the present invention according to this disclosure, that of the patents or below applications, and the knowledge and judgment of one skilled in the art.

Such patents include, but are not limited to, U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angle rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142743 entitled Medical laser having controlled-temperature and sterilized fluid output; App. Pub. 20060099548 entitled Caries detection using timing differentials between excitation and return pulses; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled entitled Electromagnetic energy distributions for electromagnetically induced mechanical cutting.

All of the contents of the preceding published applications are incorporated herein by reference in their entireties.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. As iterated above, any feature or combination of features described and referenced herein are included within the scope of the present invention provided that the features included in any such combination are not mutually inconsistent as will be apparent from the context, this specification, and the knowledge of one of ordinary skill in the art. For example, any of the radiation outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Accordingly, the present invention is not intended to be limited by the disclosed embodiments, but is to be defined by such embodiments and by reference to the following claims.

What is claimed is:

1. An endodontic probe having an elongate body sized to fit within a root canal passage, the elongate body including a body proximal region, a body distal region and a body longitudinal axis extending between the body proximal region and the body distal region, the endodontic probe comprising:
    (a) an electromagnetic radiation emitting fiber optic tip disposed at the body distal region, the fiber optic tip having a distal end and a radiation emitting region disposed proximally of the distal end, the radiation emitting region being structured to emit a peak concentration of radiation along a line that is not parallel to the body longitudinal axis; and
    (b) a porous structure characterized by one or more of (i) encompassing a region of the fiber optic tip excluding the radiation emitting region and (ii) comprising a material that is transparent to a wavelength of energy carried by the electromagnetic radiation emitting fiber optic tip, the porous structure comprising pores that are loaded with a biofluid or biopowder, the biofluid or biopowder comprising one or more of biologically-active particles, cleaning particles, biologically-active agents, and cleaning agents that are structured to be delivered from the porous structure onto tissue.

2. The endodontic probe as set forth in claim 1, wherein the porous structure is a porous wall which is an integral, non-removable part of the fiber optic tip.

3. The endodontic probe as set forth in claim 1, wherein the porous structure covers a region of the fiber optic tip distally of the radiation emitting region.

4. The endodontic probe as set forth in claim 1, wherein the porous structure is secured to and can be retracted and removed from the endodontic probe while inside of a dentinal canal.

5. The endodontic probe as set forth in claim 1, wherein the electromagnetic radiation emitting fiber optic tip is coupled to one or more of an infrared laser and a near-infrared laser.

6. The endodontic probe as set forth in claim 1, wherein the radiation emitting region is structured to emit a greater concentration in a non-distal direction than in a distal direction.

7. The endodontic probe as set forth in claim 1, wherein the radiation emitting region comprises a longitudinal axis and is structured to emit a peak concentration of radiation along a line that is not parallel to the longitudinal axis.

8. The endodontic probe as set forth in claim 1, wherein the particles or agents comprise cleaning particles.

9. The endodontic probe as set forth in claim 1, wherein the particles or agents comprise anesthetizing particles.

10. The endodontic probe as set forth in claim 1, wherein the particles or agents comprise disinfectant particles.

11. The endodontic probe as set forth in claim 1, wherein the particles or agents are suspended in a liquid.

12. The endodontic probe as set forth in claim 1, wherein liquid has a viscosity greater than that of water.

13. The endodontic probe as set forth in claim 1, wherein the porous structure comprises a sheath.

14. The endodontic probe as set forth in claim 1, wherein the porous structure comprises a fabric.

15. The endodontic probe as set forth in claim 1, wherein the porous structure comprises a sponge.

16. The endodontic probe as set forth in claim 1, wherein the porous structure comprises a membrane disposed around at least a part of the electromagnetic radiation emitting fiber optic tip.

17. The endodontic probe as set forth in claim 1, and further comprising a fluid output.

18. The endodontic probe as set forth in claim 1, a portion of the electromagnetic radiation emitting fiber optic tip disposed proximally of the distal end comprising a jacket, and the distal end not comprising the jacket.

19. The endodontic probe as set forth in claim 1, the porous structure comprising a sponge or sheath formed in a compact, low-profile fashion for providing minimally invasive access to a surgical site of tissue comprising one or more of a canal, a pocket, and a periodontal pocket.

20. The endodontic probe as set forth in claim 1, the porous structure comprising a sponge or sheath formed to expand and allow the release of biofluids or biopowders to a target site upon placement into contact with a fluid in a mouth.

* * * * *